United States Patent
Brazdil et al.

(10) Patent No.: US 11,414,376 B2
(45) Date of Patent: Aug. 16, 2022

(54) DEHYDRATION AND AMINATION OF ALPHA-, BETA-DIHYDROXY CARBONYL COMPOUNDS TO ALPHA-AMINO ACIDS

(71) Applicant: Archer Daniels Midland Company, Decatur, IL (US)

(72) Inventors: James Brazdil, Glen Ellyn, IL (US); Donald Rogness, Del Mar, CA (US); Chi-Cheng Ma, Champaign, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 27 days.

(21) Appl. No.: 17/046,730

(22) PCT Filed: Apr. 2, 2019

(86) PCT No.: PCT/US2019/025281
§ 371 (c)(1),
(2) Date: Oct. 9, 2020

(87) PCT Pub. No.: WO2019/199518
PCT Pub. Date: Oct. 17, 2019

(65) Prior Publication Data
US 2021/0163400 A1   Jun. 3, 2021

Related U.S. Application Data

(60) Provisional application No. 62/657,404, filed on Apr. 13, 2018.

(51) Int. Cl.
*C07C 227/08* (2006.01)
*B01J 23/46* (2006.01)
(Continued)

(52) U.S. Cl.
CPC .......... *C07C 227/08* (2013.01); *B01J 23/462* (2013.01); *B01J 21/18* (2013.01); *C07C 51/02* (2013.01);
(Continued)

(58) Field of Classification Search
None
See application file for complete search history.

(56) References Cited

U.S. PATENT DOCUMENTS

2016/0122288 A1* 5/2016 Gruenanger .......... C07C 227/08
562/575

FOREIGN PATENT DOCUMENTS

CN        104803841   *  7/2015 ............ B01J 23/002

OTHER PUBLICATIONS

Yu ("Tungsten complex induced dehydration of 2,3-dihydroxycarboxylic acids to alpha-keto-acids" Tetrahedron Letters, 1992, 35(45), p. 6791-6791) (Year: 1992).*

(Continued)

*Primary Examiner* — Amy C Bonaparte
(74) *Attorney, Agent, or Firm* — William B. Miller

(57) ABSTRACT

Processes are disclosed for the synthesis of an α-amino acid or α-amino acid derivative, from a starting compound or substrate having a carbonyl functional group (C=O), with hydroxy-substituted carbon atoms at alpha (α) and beta (β) positions, relative to the carbonyl functional group. According a particular embodiment, an α-, β-dihydroxy carboxylic acid or carboxylate is dehydrated to form a dicarbonyl intermediate by transformation of the α-hydroxy group to a second carbonyl group (adjacent a carbonyl group of the starting compound) and removal of the β-hydroxy group. The dicarbonyl intermediate is optionally cracked to form a second, in this case cracked, dicarbonyl intermediate having fewer carbon atoms relative to the dicarbonyl intermediate (Continued)

but preserving the first and second carbonyl groups. Either or both of the dicarbonyl intermediate and the cracked dicarbonyl intermediate may be aminated to convert the second carbonyl group to an amino (—NH$_2$) group, for producing the corresponding α-amino acid(s).

9 Claims, 1 Drawing Sheet

(51) Int. Cl.
    *B01J 21/18*     (2006.01)
    *C07C 215/08*     (2006.01)
    *C07C 51/02*     (2006.01)
    *C07C 51/353*     (2006.01)
    *C07C 51/373*     (2006.01)
    *C07C 51/41*     (2006.01)
    *C07C 51/377*     (2006.01)

(52) U.S. Cl.
    CPC .......... *C07C 51/353* (2013.01); *C07C 51/373* (2013.01); *C07C 51/377* (2013.01); *C07C 51/41* (2013.01); *C07C 51/412* (2013.01); *C07C 215/08* (2013.01)

(56) References Cited

OTHER PUBLICATIONS

Howard ("Pyruvic Acid" Organic Syntheses, Coll. vol. 1, p. 475, 1941) (Year: 1941).*

Kishida ("Formation of lactic acid from glycolaldehyde by alkaline hydrothermal reaction" Carbohydrate Research, 341, 2006, p. 2619-2623) (Year: 2006).*

* cited by examiner

DEHYDRATION AND AMINATION OF ALPHA-, BETA-DIHYDROXY CARBONYL COMPOUNDS TO ALPHA-AMINO ACIDS

CROSS-REFERENCE TO RELATED APPLICATIONS

This application is a national stage entry of International Application No. PCT/US19/25281, filed Apr. 2, 2019, which itself claims priority to U.S. Provisional Patent Application No. 62/657,404, filed Apr. 13, 2018, the contents of each are incorporated herein by reference.

FIELD OF THE INVENTION

The present invention relates to synthesis methods for α-amino acids and α-amino acid derivatives, from α-, β-dihydroxy carbonyl starting compounds, including α-, β-dihydroxy carboxylic acids and carboxylates such as products obtained from glucose.

BACKGROUND OF THE INVENTION

Amino acids are the building blocks for protein synthesis and have a number of commercial uses, particularly as nutritional supplements. One important application resides in the use of amino acids as additives of animal feeds. This is due to the low levels, or in some cases the complete lack, of certain essential amino acids in the primary constituents of such feeds, such as soybeans. Amino acids are currently indispensable ingredients for improving the efficiency in the natural (biological) production of animal protein (e.g., in the form of meat and milk), and for generally increasing the overall supply of such high value protein.

Strategies for the synthesis of amino acids based on both microbial fermentation and chemical synthesis continue to evolve, leading to cost reductions that have fueled a continued expansion of the market for these protein components. Some conventional, non-fermentative synthesis routes have utilized cyanides that lead to apparent safety concerns. More recently, pathways have been proposed in US 2004/092725 and US 2013/0158294 with carboxylic acids as starting materials, which are based on oxidation/amination of hydroxy groups at various positions, and particularly at the α-carbon position in the case of the latter publication.

There remains a need in the art for alternative chemical synthesis strategies for amino acids, and particularly strategies involving readily available or obtainable substrates and having the flexibility of synthesizing a number of different amino acid products with commercially attractive yields.

SUMMARY

Aspects of the invention are associated with the discovery of amino acid synthesis methods that can utilize substrates such as gluconic acid and glucaric acid, which are readily derived, for example from the oxidation of glucose. Advantageously, in the case of such carboxylate (carboxylic acid) substrates or starting compounds, they may potentially exhibit greater stability compared to their precursor aldehydes (e.g., glucose). Under high temperature reaction conditions, this stability can lead to increased reaction selectivity and yield along a desired reaction sequence leading to the production of one or more defined amino acids. Product losses due to undesired side reactions are thereby reduced. Obtaining such substrates from the oxidation of aldehyde precursors to carboxylates is straightforward and inexpensive, generally requiring only air as an oxidizing agent. Particular aspects are associated with the ability of the carboxylate anion-containing substrates to coordinate with cations in solution, and particularly the ammonium cation ($NH_4^+$), to promote the formation of an imino (=NH), and ultimately amino (—$NH_2$), functional group of a number of commercially desirable α-amino acids, including alanine, serine, and methionine.

Further aspects relate to optional synthesis pathways that utilize a cracking step, resulting in an α-amino acid having a lower number of carbon atoms, relative to the substrate and/or precursor of this substrate. This cracking can be regulated by the use of a cracking catalyst or promoter, as well as reaction conditions, as described herein. The extent of cracking can thereby determine the relative yields of (i) same carbon atom-numbered α-amino acids relative to the substrate (i.e., obtained without intermediate cracking), and (ii) lower carbon atom-numbered α-amino acids relative to the substrate (i.e., obtained with intermediate cracking). More particular aspects relate to the discovery of synthesis pathways, or individual reaction steps of such pathways, which may be performed non-enzymatically, meaning without the use of an enzyme (e.g., a polypeptide) in the reaction mixture. In the case of methods described herein being carried out non-enzymatically, such as using solely one or more chemical catalysts as opposed to biological catalyst(s), advantages reside in terms of allowing a wider range of possible reaction conditions, such as conditions of temperature and/or pH that would be detrimental to biological agents (e.g., would denature proteins including enzymes) but that nonetheless allow high productivities of a desired intermediate and/or end product. Other advantages may result from decreased operating costs, and particularly those otherwise associated with enzyme separation from the product, compared to the relatively lower costs associated with heterogeneous or homogeneous chemical catalyst separation. According to some embodiments, at least one of the synthesis steps described herein of (i) dehydrating the starting compound to form the dicarbonyl intermediate, (ii) cracking the dicarbonyl intermediate to form the cracked dicarbonyl intermediate, (iii) reductively aminating the dicarbonyl intermediate or the cracked dicarbonyl intermediate to produce the α-amino acid or α-amino acid derivative, is a non-enzymatic reaction step (i.e., is not catalyzed using an enzyme). Preferably, at least two of (i), (ii), and (iii) are non-enzymatic reaction steps, and more preferably all of (i), (ii), and (iii) are non-enzymatic reaction steps.

In cases of producing same carbon atom-numbered α-amino acids relative to the substrate or starting compound, representative methods comprise synthesizing 2-amino-3-deoxygluconic acid (2-amino-4,5,6-trihydroxyhexanoic acid) from gluconic acid or glucaric acid, synthesizing aspartic acid from tartaric acid, or synthesizing homoserine from erythronic acid. In cases of producing lower carbon atom-numbered α-amino acids relative to the substrate or starting compound, representative methods comprise synthesizing alanine from 4-, 5-, or 6-carbon atom-numbered substrates, for example gluconic acid or glucaric acid. In these cases, the alanine may be obtained from a reaction pathway involving a variety of possible starting compounds, with cracking to form a pyruvic acid intermediate.

Embodiments of the invention relate to methods for the synthesis of an α-amino acid or α-amino acid derivative, from a starting compound or substrate having a carbonyl functional group (C=O), with hydroxy-substituted carbon atoms at alpha (α) and beta (β) positions, relative to the carbonyl functional group. According to one reaction step, this starting compound, namely an α-, β-dihydroxy carbonyl compound, i.e., a general class of compounds that embraces α-, β-dihydroxy carboxylic acids and carboxylates, is dehydrated to form a dicarbonyl intermediate by transformation of the α-hydroxy group to a second carbonyl group (adjacent a carbonyl group of the starting compound) and removal of the β-hydroxy group. The dicarbonyl intermediate is optionally cracked to form a second, in this case cracked, dicarbonyl intermediate having fewer carbon atoms relative to the dicarbonyl intermediate but preserving the first and second carbonyl groups. Either or both of the dicarbonyl intermediate and the cracked dicarbonyl intermediate, as the case may be, are aminated (e.g., with gaseous ammonia, $NH_3$, or aqueous ammonia, $NH_4OH$), such that the second carbonyl group of the intermediate and/or cracked intermediate is converted to an amino (—$NH_2$) group, to produce the α-amino acid(s). Other aminating agents, such as substituted amines (e.g., alkylamines or dialkylamines), may likewise be used to alternatively convert the second carbonyl group to the corresponding, substituted amino group (e.g., alkylamino or dialkylamino), and thereby produce the corresponding α-amino acid derivative(s).

These and other aspects, embodiments, and associated advantages will become apparent from the following Detailed Description.

Figure 1:
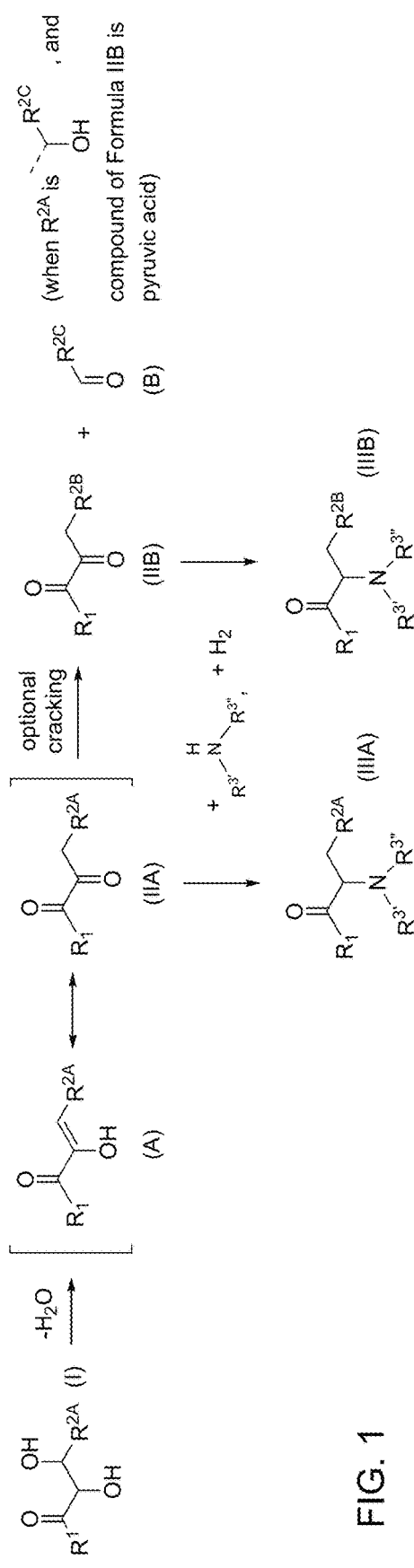
FIG. 1 illustrates a general reaction mechanism, comprising steps for synthesizing α-amino acids according to synthesis methods described herein.

The figures are to be understood to present embodiments of the invention to aid in understanding of the principles and reaction chemistry involved, but not to limit the scope of the invention as defined in the appended claims. As would be apparent to one of skill in the art having knowledge of the present disclosure, synthesis methods according to various other embodiments of the invention will utilize particular reagents and reaction conditions determined, at least in part, according to specific objectives.

DETAILED DESCRIPTION OF EMBODIMENTS

As used herein, the term "substrate," or alternatively, "starting compound," refers to the initial compound that is subjected to one or preferably a series of conversion steps, such as "dehydrating," optional "cracking," and "aminating" conversion steps, to yield an α-amino acid or α-amino acid derivative. These conversion steps do not preclude the use of prior conversion steps, such as under the same reaction conditions (e.g., in the same reactor) or under different reaction conditions (e.g., in a separate reactor), as used to produce the α-amino acid or α-amino acid derivative. Such prior conversion steps can include the conversion of a readily available precursor, such as glucose, to gluconic acid or glucaric acid as the starting compound, such as by oxidation. Likewise, a step of "producing the α-amino acid or α-amino acid derivative" does not preclude the use of subsequent conversion steps, such as under the same reaction conditions (e.g., in the same reactor) or under different reaction conditions (e.g., in a separate reactor), as used to produce the α-amino acid or α-amino acid derivative, to obtain one or more other desired end products. For example, the α-amino acid produced by the series of conversion steps may be homoserine (having an α-amino acid side chain of —$C_2H_5OH$), whereas the desired end product methionine (having an α-amino acid side chain of —$C_2H_5SCH_3$) may be obtained, for example, by the subsequent chemical conversion of the homoserine in the presence of a mercaptan compound (e.g., methylmercaptan). Methods for this conversion also include known routes based on fermentation.

The term "α-amino acid derivative" of an α-amino acid refers to any chemical compound wherein the carboxylic acid substituent of that α-amino acid may be converted to, or has the corresponding chemical structure of, an ester, aldehyde or ketone and/or the primary amine substituent of that α-amino acid is converted to, or has the corresponding chemical structure of, a secondary or tertiary amine or is replaced by another substituent which can include hydroxy, halogen among others.

The terms "mol-%" and "wt-%" are used to designate amounts or concentrations in terms of percent by mole and percent by weight, respectively. Product yields given in terms of "mol-%" refer to the moles of a given product (e.g., an α-amino acid such as alanine) obtained, based on the moles of substrate used (introduced or fed to the reactor).

The term "alkyl," when used alone or in combination with other moieties, for example, when used in combination in "alkoxy," "alkoxyalkyl," "hydroxyalkyl," "carboxyalkyl," "alkanoyl," and "alkanoylalkyl," represents a hydrocarbon moiety that is derived from an alkane. When used alone, "alkyl" therefore includes "methyl" ($CH_3$—), "ethyl" ($C_2H_5$—), etc. When used in combination, the alkyl portion of the moiety "alkoxy" is bonded at an end of the moiety to the rest of the molecule, through an intervening oxygen linkage, —O—, such as in the case of "methoxy" ($CH_3$—O—), "ethoxy" ($C_2H_5$—O—), etc., which terms are encompassed by "alkoxy." The alkyl portion of the moiety "alkanoyl" is bonded at an end of the moiety to the rest of the molecule, through an intervening carbonyl linkage, —(C═O)—, with "methanoyl" (HC═O—) representing a terminal aldehyde moiety, "ethanoyl" ($CH_3$—(C═O)—), representing methyl bonded through a carbonyl linkage, etc., which terms are encompassed by "alkanoyl."

The term "hydroxy" represents the moiety —OH, and the term "carboxy" represents the moiety —(C═O)OH. The term "hydroxyalkyl" represents hydroxy bonded at the end of the moiety to the rest of the molecule, through an intervening divalent alkyl portion, such as in the case of "hydroxymethyl" (HO—$CH_2$—), "hydroxyethyl" (HO—$C_2H_5$—), etc., which terms are encompassed by "hydroxyalkyl." The term "carboxyalkyl" represents carboxy bonded at the end of the moiety to the rest of the molecule, through an intervening divalent alkyl portion, such as in the case of "carboxymethyl" (HO—(C═O)—$CH_2$—), "carboxyethyl" (HO—(C═O)—$C_2H_5$—), etc., which terms are encompassed by "carboxyalkyl." The term "alkoxyalkyl" includes both a terminal alkoxy portion (i.e., bonded at the end of the moiety), as defined above and indicated by the designation "alkoxy," as well as an intervening divalent alkyl portion, through which "alkoxy" is bonded to the rest of the molecule. Therefore, "alkoxyalkyl" encompasses "methoxymethyl" ($CH_3$—O—$CH_2$—), "methoxyethyl" ($CH_3$—O—$C_2H_4$—), "ethoxymethyl" ($C_2H_5$—O—$CH_2$—), "ethoxyethyl" ($C_2H_5$—O—$C_2H_4$—), etc. The term "alkanoylalkyl" includes both a terminal alkanoyl portion (i.e., bonded at the end of the moiety), as defined above and indicated by the designation "alkanoyl," as well as an intervening divalent alkyl portion, through which "alkanoyl"

is bonded to the rest of the molecule. Therefore, "alkanoylalkyl" encompasses "methanoylmethyl" (H(C=O)—CH$_2$—), "methanoylethyl" (H(C=O)—C$_2$H$_4$—), "ethanoylmethyl" (CH$_3$—(C=O)—CH$_2$—), "ethanoylethyl" (CH$_3$—(C=O)—C$_2$H$_4$—), etc.

The term "optionally substituted" with respect to "alkyl," or with respect to either terminal or intervening alkyl portions of moieties as defined above, is meant to encompass the substitution of a hydrogen substituent at one or more carbon-hydrogen bonds of the alkyl or alkyl portion with the designated substituent. In the case of a substituent of hydroxy (—OH) or methyl (—CH$_3$), one, two, or three hydrogen substituents at carbon-hydrogen bonds of a terminal alkyl carbon atom may be substituted with respective —OH and/or —CH$_3$ substituents, and one or two hydrogen substituents at carbon-hydrogen bonds of an intervening (alkylene) alkyl carbon atom may be substituted with respective —OH and/or —CH$_3$ substituents. For example, in the case of a terminal alkyl portion, its terminal carbon atom may be substituted with two —CH$_3$ substituents, to yield a terminal isopropyl moiety, or may be substituted with three —CH$_3$ substituents, to yield a terminal t-butyl moiety. In the case of an intervening alkyl portion, or an intervening carbon atom of a terminal alkyl portion, one or two hydrogen substituents at carbon-hydrogen bonds of an alkylene carbon atom may be substituted with —CH$_3$ substituents to yield the corresponding methyl-substituted or dimethyl-substituted derivatives. From this description, analogous substitutions of a terminal alkyl carbon atom or intervening alkyl carbon atom with one or more —OH substituents can be appreciated. In the case of a substituent of carbonyl (=O), hydrogen substituents at two carbon-hydrogen bonds of either a terminal alkyl carbon atom or an intervening (alkylene) alkyl carbon atom may be substituted with =O, to yield a terminal aldehyde moiety (or group) or a carbonyl moiety (or group), respectively.

In view of the possible moieties and the manner in which they may be substituted, it is recognized that there may be overlap in moiety definitions, for example in the case of "methanoyl" and a terminal "methyl" being substituted with =O, both of which represent a terminal aldehyde moiety (or group). Specific moieties are mentioned, however, in order to emphasize their positive inclusion in a given compound. In addition, when "alkyl" or an "alkyl portion" is further defined with respect to its corresponding number of carbon atoms (e.g., alkyl or an alkyl portion "having from 1 to 5 carbon atoms"), optional —CH$_3$ substituents, when present, are not included in this number of carbon atoms. That is, the phrase "having from 1 to 5 carbon atoms," and other phrases defining the number of alkyl carbon atoms, refer to a backbone number of alkyl carbon atoms that may be further substituted with —CH$_3$ substituents or other substituents, according to the specific definitions given.

Carboxylic acid compounds, including amino acids, include their corresponding salt forms. In the case of a starting compound or substrate bearing a carboxylic acid functional group, the salt form is normally used in aqueous solution for carrying out the synthesis methods described herein. Corresponding salt forms of carboxylic acid include, for example, salts of alkali metals (e.g., the sodium salt form), salts of alkaline earth metals (e.g., the calcium salt form), and ammonium salts. Therefore, compounds such as "gluconic acid," "glucaric acid," "2-amino-3-deoxygluconic acid" (or "2-amino-4,5,6-trihydroxyhexanoic acid"), "aspartic acid," "tartaric acid," "homoserine," "lactic acid," etc. are meant to encompass salt forms of "gluconate," "glucarate," "2-amino-3-deoxygluconate" (or "2-amino-4,5,6-trihydroxyhexanoate"), "aspartate," "tartarate," "homoserinate," "lactate," etc. Both generic and specific structures illustrating carboxylic acid compounds are likewise meant to encompass their salt forms or ionized forms, such that the structure of gluconic acid, for example, when shown with its carboxyl group un-ionized, is meant to encompass the structure with its carboxyl group ionized, and vice versa, with the un-ionized and ionized carboxyl group of the equivalent structures of this compound shown below:

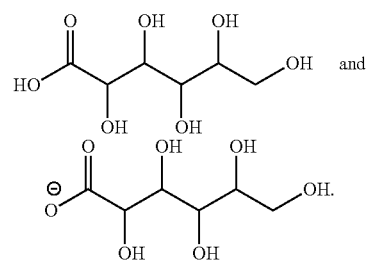

Both generic and specific structures illustrating amino acids are likewise meant to encompass forms in which their amino and/or carboxyl groups are un-ionized or ionized, with the ionization of these groups being dependent on pH, such that, for example, at pH=7.0 both the amino and carboxyl groups are normally ionized. The structure of alanine, for example, when shown with these groups being un-ionized, is meant to encompass structures with one or both of these groups being ionized, with un-ionized and ionized amino and carboxyl groups of the equivalent structures of this compound shown below:

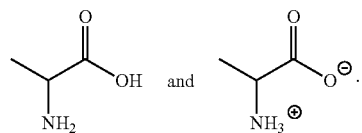

Compounds can possess one or more stereocenters, and structures are illustrated without regard for any specific stereochemistry, with the understanding that the reactions described with respect to substrates such as "gluconic acid," "glucaric acid," and "erythronic acid," which according to their nomenclature designate a specific stereochemistry, may be likewise carried out in an analogous manner with the respective, non-stereospecific substrates of "2,3,4,5,6-pentahydroxyhexanoic acid," "2,3,4,5-tetrahydroxyhexanedioic acid," and "2,3,4-trihydroxybutanoic acid," as well as with all stereoisomers of such compounds. Therefore, unless otherwise specified, "gluconic acid" is intended to encompass "gluconic acid and stereoisomers thereof," as is intended with respect to other compounds designating a specific stereochemistry. Generic and specific compounds described herein may be used or obtained in the form of pure or purified (enriched) optical isomers or otherwise in the form of racemic mixtures thereof. The use of optically active substrates or starting compounds will result in the formation of optically active products, including α-amino acids and α-amino acid derivatives, using the synthesis methods described herein, as would be appreciated by those having skill in the art, combined with knowledge from the present disclosure. Otherwise, the purification of a particular optical isomer, or enrichment in one optical isomer relative to another, can be obtained, for example, by the formation of diastereomeric salts through treatment with an optically active acid or base. Examples of appropriate acids are tartaric, diacetyltartaric, dibenzoyltartaric, ditoluoyltartaric and camphorsulfonic acid. Examples of appropriate bases are plant-derived chiral alkaloids. The mixtures of diastereomers are then separated by crystallization, followed by liberation of the optically active bases or acids from these salts. A different process for separation of optical isomers involves the use of a chiral chromatography column chosen to maximize the separation of the enantiomers. Still another available method involves synthesis of covalent diastereomeric molecules by reaction with an optically pure acid in an activated form or an optically pure isocyanate. The synthesized diastereomers can be separated by conventional means such as chromatography, distillation, crystallization or sublimation, and then hydrolyzed to yield the enantiomerically pure compound.

A general reaction mechanism for synthesizing α-amino acids is illustrated in FIG. 1. As shown, a compound of general Formula I is a starting compound that is broadly an α-, β-dihydroxy carbonyl compound, which encompasses a preferred class of compounds, namely α-, β-dihydroxy carboxylic acid or carboxylate when $R^1$ is hydroxy (—OH) to provide a terminal carboxyl group on the left-hand side of the illustrated compound. A compound of general Formula I in FIG. 1 comprises an α-hydroxy group, substituted at the α-carbon atom with respect to the carbonyl (C=O) group shown, as well as a β-hydroxy group, substituted at the β-carbon atom with respect to this carbonyl group. According to the illustrated synthesis mechanism, a first step of dehydration (water removal) causes removal of the β-hydroxy group, together with formation of a site of unsaturation, i.e., a carbon-carbon double bond between the α-carbon atom and the β-carbon atom. The resulting ethylenically unsaturated, dehydrated compound, shown as compound A, tends to maintain tautomeric equilibrium with the dicarbonyl intermediate shown as having general Formula IIA. The dehydrating step may therefore comprise forming water from a combination of the β-hydroxy group and hydrogen of the α-hydroxy group, in a starting compound or substrate of general Formula I.

Amination of this dicarbonyl intermediate with an aminating agent, or reductive aminating agent, of the formula $NHR^{3'}R^{3''}$, as shown, can produce an α-amino acid or α-amino acid derivative having the general Formula IIIA

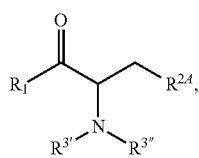
(IIIA)

as shown in FIG. 1, which may be an α-amino acid, for example in the case of $R^1$ being hydroxy (—OH) and the aminating agent being gaseous or aqueous ammonia (ammonium hydroxide), such that $R^{3'}$ and $R^{3''}$ are each hydrogen substituents. Otherwise, the compound above may be a particular α-amino acid derivative, having at least a derivatized amino group, in the case of other types of aminating agents, such as monoalkyl or dialkyl amines. For example, methylamine as an aminating agent can result in the corresponding methylamino acid derivative, in which case one of $R^{3'}$ and $R^{3''}$ may be a hydrogen substituent and the other a methyl substituent, and methylethylamine as an aminating agent can result in the corresponding methyl, ethyl diamino acid derivative, in which case one of $R^{3'}$ and $R^{3''}$ may be a methyl substituent and the other an ethyl substituent. These and other reductive aminating agents are described herein.

According to other embodiments, the dicarbonyl intermediate compound of general Formula IIA may optionally undergo cracking to form the cracked dicarbonyl intermediate of general Formula IIB. As a consequence of cracking, the moiety represented by $R^{2B}$ in the cracked dicarbonyl intermediate of general Formula IIB has fewer carbon atoms relative to the moiety represented by $R^{2A}$ in the dicarbonyl intermediate of general Formula IIA. Accordingly, the cracked dicarbonyl intermediate overall has fewer carbon atoms relative to the dicarbonyl intermediate. Amination of the cracked dicarbonyl intermediate can then produce an α-amino acid or α-amino acid derivative having the general Formula IIIB

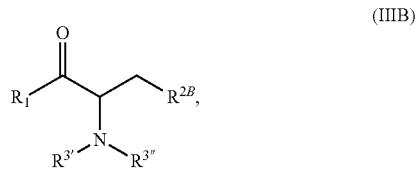
(IIIB)

as shown in FIG. 1, in an analogous manner as described above with respect to producing an α-amino acid or α-amino acid derivative having the general Formula IIIA from amination of the dicarbonyl intermediate of general Formula IIA. The optional cracking to form the cracked dicarbonyl intermediate additionally forms a second cracked species. In the embodiment illustrated in FIG. 1, this second cracked species may have the structure according to compound B, as shown and having an aldehyde group. Depending on the substrate or starting compound, this second cracked species may include other functional groups, such as a carboxylic acid functional group, as the moiety represented by $R^{2C}$, or otherwise included in a terminal portion of this moiety, which is bonded to the aldehyde functional group. Such a second cracked species may result, for example, when the moiety represented by $R^{2A}$ in the dicarbonyl intermediate of general Formula IIA is bonded through a hydroxy-substituted carbon atom. In a particular embodiment, the second cracked species of compound B may result in the case of $R^{2A}$, or at least a terminal portion of $R^{2A}$, representing a moiety of

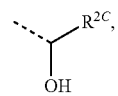

in which case the cracked dicarbonyl intermediate will have fewer carbon atoms, relative to both the dicarbonyl intermediate and the substrate. The cracked dicarbonyl intermediate may then become aminated, whereas further conversions of the second cracked species (e.g., by amination and/or hydrogenation) may form other desirable compounds, for example as described with respect to the more particular embodiment shown in FIG. 2. According to some methods, the moiety represented by $R^{2C}$ in compound B may have one fewer carbon atom, relative to the moiety represented by $R^{2A}$, and compound B may represent a corresponding aldehyde formed from $R^{2A}$ and having the same number of carbon atoms as $R^{2A}$. In this case, the cracked dicarbonyl intermediate may be pyruvic acid, which may become aminated to alanine. It can be appreciated, therefore, that a synthesis route to alanine, through cracking of the dicarbonyl intermediate to form pyruvic acid, can be carried out using a variety of α-, β-dihydroxy carbonyl compounds, including α-, β-dihydroxy carboxylic acids and carboxylates having at least four carbon atoms, as substrates.

Whether the dicarbonyl intermediate of general Formula IIA becomes aminated directly, or optionally cracked and then aminated, consumption of this dicarbonyl intermediate drives the tautomeric equilibrium toward the production of further dicarbonyl intermediate from compound A. The extent to which the dicarbonyl intermediate becomes directly aminated or optionally cracked and then aminated may be regulated by the use of a cracking catalyst or promoter, as well as reaction conditions, as described herein. In particular applications involving an intermediate cracking step, for example, a 3 carbon atom-numbered α-amino acid, such as alanine, may be produced from available 4-, 5-, or 6-carbon atom-numbered α-, β-dihydroxy carboxylic acids and carboxylates as starting compounds, such as erythronic acid (or 2,3,4-trihydroxybutanoic acid generally); 2,3-dihydroxy-4-oxobutanoic acid; tartaric acid; 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally). Other particular examples of synthesis methods with and without the use of a cracking catalyst are described herein. Often, therefore, different α-amino acids or their derivatives, having different numbers of carbon atoms, may be formed from a combination of both synthesis via a dicarbonyl intermediate and synthesis via a cracked dicarbonyl intermediate, with relative yields of the different α-amino acids or their derivatives being regulated. Alternatively, in the absence of a cracking catalyst, all or substantially all (e.g., greater than about 95 mol-%) of the α-amino acid or α-amino acid derivative produced according to the synthesis method may be via amination of the dicarbonyl intermediate of general Formula IIA, in which case this α-amino acid or α-amino acid derivative may have the same number of carbon atoms as the dicarbonyl intermediate, as well as the substrate.

With respect to compounds in FIG. 1 having the general Formulas I, IIA, IIB, IIIA, and IIIB, as well as those having the general formula given for compound A, $R^1$ may be selected from the group consisting of alkyl, alkoxy, alkoxyalkyl, hydroxy, and hydroxyalkyl, wherein alkyl and the alkyl portions of alkoxy, alkoxyalkyl, and hydroxyalkyl have from 1 to 5 carbon atoms, optionally substituted with one or more substituents (i.e., may optionally have hydrogen substituents at carbon-hydrogen bonds substituted, as defined herein, with one or more substituents) selected from the group consisting of —OH, —CH$_3$, and =O. According to particular embodiments, in these respective compounds, including the starting compound of general Formula I, the dicarbonyl intermediate and cracked dicarbonyl intermediate of general Formulas IIA and IIB, respectively, and/or the α-amino acids or α-amino acid derivatives of general Formulas IIIA or IIIB, $R^1$ may be alkyl (e.g., having from 1 to 3 alkyl carbon atoms) and may result in a terminal ketone functional group in the respective compounds; $R^1$ may be alkoxy (e.g., having from 1 to 3 alkyl carbon atoms) and may result in a terminal ester functional group in the respective compounds; or $R^1$ may be hydroxy and may result in a terminal carboxyl functional group in the respective compounds. Preferably, $R^1$ is hydroxy, whereby the starting compound and the dicarbonyl intermediate are carboxylic acids. For example, as described above with respect to terms used herein generally, the starting compound, the dicarbonyl intermediate, and the α-amino acid or α-amino acid derivative, may be in the form of (e.g., present in the reaction mixture as) carboxylates, meaning compounds comprising a carboxylate anion and possibly present in salt form in an aqueous reaction mixture (e.g., in their corresponding ammonium salt form) that is used to carry out synthesis methods described herein.

With respect to compounds in FIG. 1 having the general Formulas I, IIA, and IIIA, as well as those having the general formula given for compound A, $R^{2A}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 5 carbon atoms, optionally substituted with one or more substituents selected from the group consisting of —OH, —CH$_3$, and =O. According to a particular embodiment, $R^{2A}$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 3 carbon atoms, optionally substituted with one or more of —OH and/or one or more of —CH$_3$. According to a more particular embodiment, $R^{2A}$ may be a hydrogen substituent, alkyl, carboxy, carboxyalkyl, alkanoyl, or alkanoylalkyl, wherein alkyl and the alkyl portions of carboxyalkyl, alkanoyl, and alkanoylalkyl have from 1 to 3 carbons atoms, optionally substituted with one or more of —OH. Particular substrates having from 3-6 carbon atoms include 2,3-dihydroxy propanoic acid; erythronic acid (or 2,3,4-trihydroxybutanoic acid generally); 2,3-dihydroxy-4-oxobutanoic acid; tartaric acid; 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally).

It can be appreciated from the present disclosure that, when $R^{2A}$ is a hydrogen substituent, cracking to form a cracked dicarbonyl intermediate of general Formula IIB cannot occur. Nonetheless, an α-amino acid or α-amino acid derivative may be produced from the dicarbonyl intermediate of general Formula IIA, for example in the production of alanine from 2-,3-dihydroxy propanoic acid, in the absence of cracking.

With respect to compounds having the general Formulas IIB, and IIIB, $R^{2B}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms, optionally substituted with one or more substituents selected from the group consisting of —OH, —CH$_3$, and =O. According to a particular embodiment, $R^{2B}$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 3 carbon atoms, optionally substituted with one or more of —OH and/or one or more of —CH₃. According to a more particular embodiment, $R^{2B}$ may be a hydrogen substituent, alkyl, carboxy, carboxyalkyl, alkanoyl, or alkanoylalkyl, wherein alkyl and the alkyl portions of carboxyalkyl, alkanoyl, and alkanoylalkyl have 1 or 2 carbons atoms, optionally substituted with one or more of —OH. According to another particular embodiment, $R^{2B}$ may be a hydrogen substituent or alkyl having from 1 to 3 carbon atoms, optionally substituted with one or more of —OH.

It can be further appreciated from the present disclosure that, when $R^1$ is hydroxy and $R^{2B}$ is a hydrogen substituent, the cracked dicarbonyl intermediate is pyruvic acid that may become aminated to form alanine, potentially from a variety of possible α-, β-hydroxy carboxylate substrates, as described above. In addition, the second cracked species of compound B may result in the case of $R^{2A}$, or at least a terminal portion of $R^{2A}$, representing a moiety of

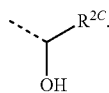

Accordingly, $R^{2C}$ in compounds having the general formula given for compound B may represent moieties as defined above with respect to $R^{2A}$, but having at least one fewer carbon atom. Therefore, $R^{2C}$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms, optionally substituted with one or more substituents selected from the group consisting of —OH, —CH₃, and =O. According to a particular embodiment, $R^{2C}$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have one or two carbon atoms, optionally substituted with one or more of —OH and/or one or more of —CH₃. According to a more particular embodiment, $R^{2C}$ may be a hydrogen substituent or alkyl having one or two carbon atoms, optionally substituted with one or more of —OH.

With respect to compounds in FIG. 1 having the general Formulas IIIA and IIIB, $R^{3'}$ and $R^{3'''}$ are independently a hydrogen substituent or alkyl, wherein alkyl has from 1 to 5 carbon atoms which may optionally be substituted with one or more substituents selected from the group consisting of —OH, —CH₃, and =O. Preferably, $R^{3'}$ and $R^{3'''}$ are independently a hydrogen substituent or alkyl having from 1 to 3 carbon atoms. More preferably, $R^{3'}$ and $R^{3'''}$ are independently a hydrogen substituent, methyl, or ethyl. Still more preferably $R^{3'}$ and $R^{3'''}$ are both a hydrogen substituent.

A typical reaction environment associated with the synthesis of an α-amino acid or α-amino acid derivative, according to methods described herein, includes an elevated hydrogen partial pressure, such as a hydrogen partial pressure of at least about 3 megapascals (MPa) (435 psi), optionally in combination with a hydrogenation catalyst. In this hydrogenating/reducing environment, the terminal aldehyde group in the second cracked species of compound B may be converted to a terminal alcohol or hydroxy (—OH) group. Furthermore, this terminal hydroxy group and/or one or more other hydroxy groups present in this second cracked species, and more particularly present in the moiety $R^{2C}$, may be converted to the corresponding amino or substituted amino group, depending on the type(s) and amount(s) of one or more aminating agents present in the reaction environment. Therefore, a number of possible conversion products of the second cracked species are possible, as described in greater detail below with respect to the more particular embodiment shown in FIG. 2.

Figure 2:
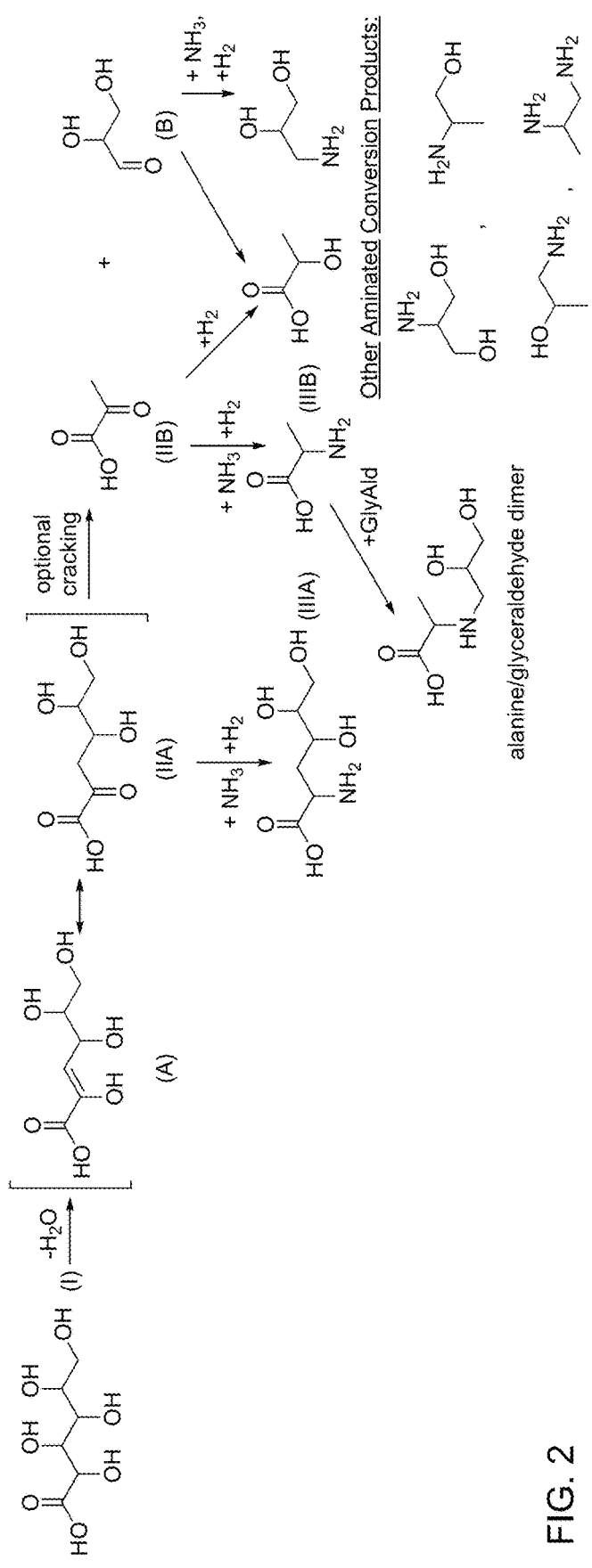
FIG. 2 illustrates a specific reaction mechanism, according to which gluconic acid is the starting material or substrate, with specific byproducts also shown.

FIG. 2 illustrates the synthesis method presented in FIG. 1, using gluconic acid (or generally 2,3,4,5,6-pentahydroxyhexanoic acid) as a starting compound, or compound of Formula I, in which $R^{2A}$ represents the moiety

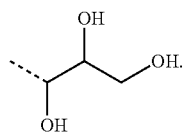

In this embodiment, the dicarbonyl intermediate of Formula IIA is 2-keto-3-deoxygluconic acid (2-keto-4,5,6-trihydroxyhexanoic acid), as shown. This dicarbonyl intermediate can then undergo amination with gaseous or aqueous ammonia to yield an α-amino acid, having the same number of carbon atoms relative to the starting compound. In this case, this α-amino acid is 2-amino-3-deoxygluconic acid (2-amino-4,5,6-trihydroxyhexanoic acid), which is shown as the compound having Formula IIIA. Alternatively, or in combination, the dicarbonyl intermediate can undergo cracking to yield a cracked dicarbonyl intermediate of Formula IIB, which in the embodiment illustrated in FIG. 2 is pyruvic acid. Amination of this cracked dicarbonyl intermediate then provides a pathway to a different α-amino acid, having fewer carbon atoms relative to the starting compound. In this case, this different α-amino acid is alanine, shown as the compound having Formula IIIB. In addition, cracking to form pyruvic acid additionally forms a second cracked species of compound B, in this case is glyceraldehyde, according to which $R^{2C}$ in the general formula for this compound as shown in FIG. 1, is a moiety of

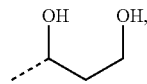

which corresponds to the moiety of $R^{2A}$ as shown above, but having one fewer carbon atom.

Further potential reaction products are also possible under reaction conditions described herein, as shown in FIG. 2. For example, hydrogenation/reduction of pyruvic acid, the cracked dicarbonyl intermediate of Formula IIB, can yield lactic acid. Hydrogenation/reduction of glyceraldehyde, the second cracked species of compound B, can yield glycerol (not shown), or otherwise hydrogenation/reduction may be combined with amination, for example with gaseous or aqueous ammonia, to yield 2-,3-dihydroxy propylamine and/or other aminated conversion products such as various amino- and/or hydroxy-substituted derivatives of propanol or propylamine (e.g., hydroxypropylamines), as shown in FIG. 2. In addition, glyceraldehyde, the second cracked species of compound B, can undergo further reactions, such as those involving a 1,2-hydride shift or a hydride transfer (Cannizzaro reaction) to cause its conversion to lactic acid, as shown in FIG. 2. Furthermore, glyceraldehyde can combine with alanine to form an alanine/glyceraldehyde dimer, as also shown. Therefore, according to particular embodiments, alanine and lactic acid may be produced in a combined molar amount that exceeds a net molar amount of glyceraldehyde produced, despite the fact that the cracking reaction may yield equimolar amounts of pyruvic acid (which may become aminated to produce alanine or hydrogenated to produce lactic acid) and glyceraldehyde. For example, the ratio of the combined molar amount of alanine and lactic acid to the net molar amount of glyceraldehyde (e.g., in the reaction mixture after completion of a synthesis method), may be at least about 1.2, at least about 1.5, or at least about 2.0. This excess may result, at least in part, due to the conversion of glyceraldehyde to lactic acid.

Other specific examples of the synthesis method presented in FIG. 1 are summarized in Table 1 below, according to particular substrates or starting compounds of Formula I, the dicarbonyl intermediate of Formula IIA, the α-amino acid of Formula IIIA, the cracked dicarbonyl intermediate of Formula IIB, the α-amino acid of Formula IIIB, and the second cracked species of compound B.

the reaction mixture, such as tungstate, molybdate, or vanadate salts, which include a metatungstate salt, a paratungstate salt, a metamolybdate salt, a paramolybdate salt, a metavanadate salt, or a paravanadate salt. Representative tungstate salts are salts of Group 1 (alkali) metals or Group 2 (alkaline earth) metals, as well as ammonium salts. Ammonium metatungstate and ammonium paratungstate salts are representative. A cracking catalyst (e.g., ammonium metatungstate) may be present in the reaction mixture in an amount of from about 0.1 mol-% to about 30 mol-%, from about 0.5 mol-% to about 10 mol-%, or from about 1 mol-% to about 5 mol-%, relative to the number of moles of substrate, for example according to the initial reactor loading composition in the case of a batchwise reaction or according to a steady-state composition in the case of a continuous reaction. The cracking catalyst may also, or may alternatively, be present in the reaction mixture in an amount such that the moles of cracking active metal (e.g., tungsten, molybdenum, or vanadium) may represent from about 6 mol-% to about 50 mol-%, or from about 10 mol-% to about 35 mol-%, relative to the number of moles of substrate.

TABLE 1

| substrate (I) | dicarbonyl intermediate (IIA) | α-amino acid (IIIA) | cracked dicarbonyl (IIB) | α-amino acid (IIIB) | cracked species (B) |
| --- | --- | --- | --- | --- | --- |
| glucaric acid, or 2,3,4,5-tetrahydroxyhexane dioic acid | 2-keto-3-deoxyglucaric acid, or 2,3-dihydroxy-5-oxohexanedioic acid | 2-amino-3-deoxyglucaric acid, or 5-amino-2,3-dihydroxyhexane dioic acid | pyruvic acid | alanine | glyceric acid |
| 2,3,4,5-tetrahydroxy-6-oxohexanoic acid | 4,5-dihydroxy-2,6-dioxohexanoic acid | 2-amino-4,5-dihydroxy-6-oxo hexanoic acid | pyruvic acid | alanine | 2-hydroxy malonaldehyde |
| 2,3,4,5-tetrahydroxypentanoic acid | 4,5-dihydroxy-2-oxopentanoic acid | 2-amino-4,5-dihydroxypentanoic acid | pyruvic acid | alanine | 2-hydroxy acetaldehyde |
| 2,3,4-trihydroxy-5-oxopentanoic acid | 4-hydroxy-2,5-dioxopentanoic acid | 2-amino-4-hydroxy-5-oxopentanoic acid | pyruvic acid | alanine | oxalaldehyde |
| 2,3,4-trihydroxypentane dioic acid | 2-hydroxy-4-oxopentane dioic acid | 2-amino-4-hydroxypentane dioic acid | pyruvic acid | alanine | 2-oxoacetate |
| erythronic acid, or 2,3,4-trihydroxybutanoic acid | 2-keto-3-deoxyerythronic acid, or 4-hydroxy-2-oxobutanoic acid | homoserine | pyruvic acid | alanine | formaldehyde/ methanol |
| 2,3-dihydroxy-4-oxobutanoic acid | 2,4-dioxobutanoic acid | 2-amino-4-oxobutanoic acid | pyruvic acid | alanine | formic acid/ methanol |
| tartaric acid | 2-keto-3-deoxytartaric acid | aspartic acid | pyruvic acid | alanine | formic acid/ methanol |
| 2,3-dihydroxy propanoic acid | 2-keto,3-hyroxy propanoic acid | alanine | (none) | | |

Representative synthesis methods therefore comprise reacting an α-, β-dihydroxy carboxylic acid or carboxylate starting compound in a reaction mixture, to form an α-amino acid or α-amino acid derivative having the same number of carbon atoms, relative to the starting compound, and/or to form an α-amino acid or α-amino acid derivative having fewer carbon atoms, relative to the starting compound. In the case of the α-amino acid or α-amino acid derivative having fewer carbon atoms, the reaction mixture preferably comprises a cracking catalyst or promoter of the reaction step shown as "optional cracking" in FIGS. 1 and 2. Preferred cracking catalysts comprise one or more cracking active metals, such as tungsten, molybdenum, and/or vanadium, which may be present in the form of corresponding salts in Other cracking catalysts can include solid acids and/or Lewis acids (e.g., organometallic compounds, including organotin compounds).

In the case of using a cracking catalyst, particular methods comprise synthesizing alanine from an α-, β-dihydroxy carboxylate starting compound having greater than 3 carbon atoms, such as a salt of gluconate (or 2,3,4,5,6-pentahydroxyhexanoate generally); 2,3,4,5-tetrahydroxy-6-oxohexanoate; glucarate (or 2,3,4,5-tetrahydroxyhexanedioate generally); 2,3,4,5-tetrahydroxypentanoate; 2,3,4-trihydroxy-5-oxopentanoate; 2,3,4-trihydroxypentanedioate; erythronate (or 2,3,4-trihydroxybutanoate generally); 2,3-dihydroxy-4-oxobutanoate; or tartarate. As described herein, such methods comprise dehydrating this starting compound to form a dicarbonyl intermediate by transformation of the alpha hydroxy group to a second carbonyl group and removal of the beta hydroxy group, and cracking this dicarbonyl intermediate to form pyruvate. The pyruvate is then aminated to produce the alanine.

As described above, the cracking catalyst can be used to regulate the relative yields of (i) α-amino acids and/or α-amino acid derivatives having the same number of carbon atoms relative to the substrate and obtained from a synthesis pathway that does not include cracking and (ii) α-amino acids and/or α-amino acid derivatives having fewer carbon atoms relative to the substrate and obtained from a synthesis pathway that includes cracking. According to particular embodiments in which the cracking catalyst (e.g., tungsten-containing compound) is absent from the reaction mixture, the yield(s) of α-amino acids and/or α-amino acid derivatives according to (i) above may account for at least about 85 mol-%, or even at least about 95 mol-%, of the molar yield(s) of all α-amino acids and/or α-amino acid derivatives produced. According to particular embodiments in which the cracking catalyst (e.g., tungsten-containing compound) is present in the reaction mixture, the molar yield(s) of α-amino acids and/or α-amino acid derivatives according to (ii) above may account for at least about 50 mol-% (e.g., from about 50 mol-% to about 95 mol-%), or at least about 75 mol-% (e.g., from about 70 mol-% to about 90 mol-%), of the molar yield(s) of all α-amino acids and/or α-amino acid derivatives produced. Regardless of whether a cracking catalyst is present in the reaction mixture, the total yield(s) of α-amino acids and/or α-amino acid derivatives according to (i) above and/or the total yield(s) of α-amino acids and/or α-amino acid derivatives according to (ii) above, based on the theoretical yields proceeding through the respective non-cracking pathway (i) or optional cracking pathway (ii), may be generally at least about 25 mol-% (e.g., from about 25 mol-% to about 90 mol-%), typically at least about 35 mol-% (e.g., from about 35 mol-% to about 80 mol-%), and often at least about 50 mol-% (e.g., from about 50 mol-% to about 75 mol-%). These yields can apply, for example, to any of the α-amino acids and/or α-amino acid derivatives according to general Formulas IIIA and IIIB described herein, including the specific α-amino acids and/or α-amino acid derivatives described herein (e.g., alanine) as products of the synthesis.

The reaction mixture, which is preferably an aqueous reaction mixture, may further comprise an aminating agent such as gaseous or aqueous ammonia (ammonium hydroxide) as described above, and/or otherwise possibly an alkylated amine such as a compound of the formula $NHR^{3'}R^{3''}$, wherein $R^{3'}$ and $R^{3''}$ are as defined herein, e.g., with respect to compounds according to Formula IIIA and IIIB. Other ammonium salts, such as ammonium halides, may also be used in place of, or in combination with, ammonium hydroxide. One or more ammonium salts (e.g., ammonium hydroxide and/or ammonium chloride) may be present as a solution in a concentration, or combined concentration, from about 10 wt-% to about 50 wt-%, or from about 15 wt-% to about 35 wt-%. In general, the amount of solution comprising such ammonium salt(s) is at least sufficient to solubilize the substrate, cracking catalyst (if used), and any additives, in an aqueous solution as the reaction mixture.

The reaction mixture may further comprise a hydrogenation catalyst, such as solid (heterogeneous) catalyst. A representative hydrogenation catalyst may comprise one or more hydrogenation active metals selected from Groups 8-11 of the Periodic Table, such as, for example, ruthenium (Ru), cobalt (Co), nickel (Ni), platinum (Pt), palladium (Pd), or gold (Au). A preferred hydrogenation active metal is ruthenium. The catalyst may further comprise a solid support of the hydrogenation active metal(s), with the metals being dispersed on the solid support according to a distribution, for example preferentially near the outer surface of the solid support or otherwise substantially uniformly throughout a porous solid support, depending on the particular catalyst preparation technique used (e.g., evaporative impregnation of a solution of the hydrogenation active metal). Preferably, the hydrogenation active metal, or such metals in combination, is/are present in an amount from about 1 wt-% to about 15 wt-%, or from about 2 wt-% to about 10 wt-%, based on the total weight of the hydrogenation catalyst.

The hydrogenation active metal(s) may also, or may alternatively, be present in the reaction mixture in an amount such that the moles of hydrogenation active metal(s) (e.g., ruthenium) represent from about 1 mol-% to about 20 mol-%, or from about 2 mol-% to about 10 mol-%, relative to the number of moles of substrate, for example according to the initial reactor loading composition in the case of a batchwise reaction or according to steady-state composition in the case of a continuous reaction. The solid support is preferably refractory in the reaction mixture and under the synthesis reaction conditions described herein. Representative solid supports comprise one or more metal oxides, such as aluminum oxide (alumina), silicon oxide (silica), titanium oxide (titania), zirconium oxide (zirconia), magnesium oxide (magnesia), strontium oxide (strontia), etc. A preferred solid support is carbon. According to a particular embodiment, the hydrogenation catalyst comprises ruthenium on a carbon support, with the ruthenium being present in an amount within a range given above, based on total catalyst weight and/or within a range given above, relative to the number of moles of substrate.

Reaction conditions, under which the reaction mixture is maintained during the synthesis of the α-amino acid and/or α-amino acid derivative, include an elevated pressure and hydrogen partial pressure. Representative absolute reactor pressures are in the range generally from about 2.07 MPa (300 psi) to about 24.1 MPa (3500 psi), typically from about 3.45 MPa (500 psi) to about 20.7 MPa (3000 psi), and often from about 10.3 MPa (1500 psi) to about 17.2 MPa (2500 psi). The reactor pressure may be generated predominantly or substantially from hydrogen, such that these ranges of total pressure may also correspond to ranges of hydrogen partial pressure. However, the presence of gaseous ammonia or other aminating agent, as well as other gaseous species vaporized from the reaction mixture, may result in the hydrogen partial pressure being reduced relative to these total pressures, such that, for example, the hydrogen partial pressure may range generally from about 1.38 MPa (200 psi) to about 22.4 MPa (3250 psi), typically from about 2.41 MPa (350 psi) to about 19.0 MPa (2750 psi), and often from about 8.62 MPa (1250 psi) to about 15.5 MPa (2250 psi).

Other reaction conditions include a temperature from about 100° C. to about 350° C., and preferably from about 130° C. to about 230° C. The reaction time, i.e., time at which the reaction mixture is maintained under conditions of pressure and temperature at any target values or target sub-ranges within any of the ranges of pressure and temperature given above (e.g., a target, total pressure value of 13.8 MPa (2000 psi) and a target temperature of 160° C.), is from about 0.5 hours to about 24 hours, and preferably from about 1 hour to about 5 hours, in the case of a batchwise reaction. For a continuous reaction, these reaction times correspond to reactor residence times. Continuous operation may be performed, for example, under the conditions of pressure and temperature described above, with continuous feeding of the substrate, aminating agent, and hydrogen, and continuous withdrawal of the reaction mixture comprising the α-amino acid or α-amino acid derivative. Continuous operation may further include the continuous purification of the α-amino acid or α-amino acid derivative, the continuous separation of process streams comprising unconverted gaseous and/or liquid products, and/or the continuous recycle of one or more of such process streams back to the reaction mixture, maintained in the synthesis reactor. In the case of recycle operation, the yields of the α-amino acid or α-amino acid derivative, as described above, will correspond to the "once-through" or "per-pass" yield, with higher overall yields being possible due to the recycle.

The following examples are set forth as representative of the present invention. These examples are not to be construed as limiting the scope of the invention as other equivalent embodiments will be apparent in view of the present disclosure and appended claims.

Example 1

An experiment was conducted to investigate the conversion of gluconic acid to alanine, according to a synthesis method described herein. An initial, 10 gram (45.9 mmol) charge of gluconic acid, sodium salt (Sigma, 99+ wt-%) was weighed and added to a 300 ml Parr reactor, together with 9.27 grams of a solid, carbon-supported ruthenium hydrogenation catalyst (5 wt-% Ru, BASF), providing 5 mol-% Ru, relative to the gluconic acid substrate (assuming 50 wt-% moisture content of the catalyst). Also weighed and added to the reactor was 2.5 grams ($0.85 \times 10^{-4}$ moles) of ammonium metatungstate hydrate $(NH_4)_6H_2W_{12}O_{40} \cdot x H_2O$ (Fluka, 99+ wt-%), corresponding to about 2 mol-% of this cracking catalyst and about 20 mol-% of tungsten in this cracking catalyst, relative to the moles of substrate. In addition to these components, 100 ml of 28 wt-% ammonium hydroxide solution was added to the Parr reactor as a solvent and also as an aminating agent. The initial reaction mixture (initial reactor loading composition) therefore included the substrate, hydrogenation catalyst, cracking catalyst, and aminating agent.

The reaction mixture was then sealed, and stirring (500-600 rpm) was initiated. The Parr reactor was pressurized to below the target pressure of 13.8 MPa (2000 psi), and the reaction mixture was heated to a target temperature of 200° C. Upon achieving this target (reaction) temperature, the pressure was increased to the target value, marking the starting point for the reaction time of 2 hours. The reaction mixture was allowed to stir under these conditions of pressure and temperature for this reaction time, after which the reaction mixture was cooled to below 80° C. and depressurized. The reaction mixture was then filtered to remove solids, and vial samples were submitted for composition analysis by gas chromatography-mass spectrometry (GC-MS).

Example 2

A second experiment was conducted according to the procedures described in Example 1, except that the reaction temperature was 160° C.

Example 3

A third experiment was conducted according to the procedures described in Example 1, except that the reaction temperature was 160° C., and 1.85 grams of a solid, carbon-supported ruthenium hydrogenation catalyst (5 wt-% Ru, BASF) was used, providing 1 mol-% Ru, relative to the gluconic acid substrate (assuming 50 wt-% moisture content of the catalyst).

Example 4

A fourth experiment was conducted according to the procedures described in Example 1, except that the reaction temperature was 180° C., and 4.64 grams of a solid, carbon-supported ruthenium hydrogenation catalyst (5 wt-% Ru, BASF) was used, providing 2.5 mol-% Ru, relative to the gluconic acid substrate (assuming 50 wt-% moisture content of the catalyst).

Example 5

A fifth experiment was conducted according to the procedures described in Example 1, except that the reaction temperature was 160° C., and the reaction time was 24 hours.

Example 6

A sixth experiment was conducted according to the procedures described in Example 1, except that the reaction temperature was 180° C., and 4.64 grams of a solid, carbon-supported ruthenium hydrogenation catalyst (5 wt-% Ru, BASF) was used, providing 2.5 mol-% Ru, relative to the gluconic acid substrate (assuming 50 wt-% moisture content of the catalyst). Also, an additive of 0.25 grams of ammonium acetate, or 7 mol-% relative to the substrate, was included in the initial reaction mixture.

Example 7

A seventh experiment was conducted according to the procedures described in Example 1, except the reaction pressure was 8.96 MPa (1300 psi) and the reaction temperature was 180° C. Also, 4.64 grams of a solid, carbon-supported ruthenium hydrogenation catalyst (5 wt-% Ru, BASF) was used, providing 2.5 mol-% Ru, relative to the gluconic acid substrate (assuming 50 wt-% moisture content of the catalyst). Also, an additive of 1.10 grams of LiOH, or 1 molar equivalent relative to the substrate, was included in the initial reaction mixture.

For the above Examples 1-7, the synthesis conditions and mol-% yield of alanine, calculated from the results obtained from GC-MS, are summarized in Table 2 below. From the description of these experiments, it can be appreciated that common characteristics were the use of (i) 10 grams (45.9 mmol) of gluconic acid, sodium salt as the substrate, (ii) a solid, carbon-supported ruthenium hydrogenation catalyst (5 wt-% Ru, BASF), (iii) ammonium metatungstate, corresponding to about 2 mol-% relative to the moles of substrate, and (iv) 100 ml of 28 wt-% ammonium hydroxide solution as the solvent and aminating agent.

TABLE 2

| | | Reaction Conditions/Mixture Component(s) | | | | |
|---|---|---|---|---|---|---|
| Example | Alanine Yield, (mol-%) | Temperature, (° C.) | Time, (hr) | Pressure, (psi) | Ru, (mol-%) | Additive |
| 1 | 53.4 | 200 | 2 | 2000 | 5 | |
| 2 | 20.0 | 160 | 2 | 2000 | 5 | |

TABLE 2-continued

| | | Reaction Conditions/Mixture Component(s) | | | | |
|---|---|---|---|---|---|---|
| Example | Alanine Yield, (mol-%) | Temperature, (° C.) | Time, (hr) | Pressure, (psi) | Ru, (mol-%) | Additive |
| 3 | 20.6 | 160 | 2 | 2000 | 1 | |
| 4 | 54.7 | 180 | 2 | 2000 | 2.5 | |
| 5 | 56.0 | 160 | 24 | 2000 | 5 | |
| 6 | 56.5 | 180 | 2 | 2000 | 2.5 | 7 mol-% NH$_4$(COOH) |
| 7 | 46.4 | 180 | 2 | 1300 | 2.5 | 1 molar equivalent LiOH |

As can been seen from these results, significant yields of alanine were produced under all of the reaction conditions and with the reaction mixture components as described in Examples 1-7. It is expected that process optimization, based on the teachings herein, can be conducted to increase the yields of alanine, as well as optimize yields of alanine and other α-amino acids and their derivatives, using gluconic acid and other starting compounds according to the synthesis methods and overall teachings set forth in the present disclosure.

Overall, aspects of the invention relate to the use of synthesis methods described herein to produce α-amino acids and/or α-amino acids derivatives from readily available, or easily derived, substrates. The methods may advantageously address various shortcomings of conventional methods. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modifications and/or substitutions without departing from the scope of this disclosure. The specific embodiments illustrated and described herein are for illustrative purposes only, and not limiting of the invention as set forth in the appended claims.

The invention claimed is:

1. A method for synthesizing an α-amino acid or α-amino acid derivative, the method comprising:
reacting an α-, β-dihydroxy carboxylate starting compound in a reaction mixture under hydrogen pressure and comprising an aminating agent and a cracking catalyst, to form the α-amino acid or α-amino acid derivative,
wherein the α-amino acid or α-amino acid derivative has fewer carbon atoms, relative to the starting compound.

2. The method of claim 1, wherein the reaction mixture is under a hydrogen partial pressure of at least about 3 MPa (435 psi).

3. The method of claim 1, wherein the aminating agent is gaseous or aqueous ammonia, or an ammonium salt.

4. The method of claim 1, wherein the cracking catalyst comprises tungsten, molybdenum, or vanadium.

5. The method of claim 1, wherein the reaction mixture further comprises a hydrogenation catalyst.

6. The method of claim 5, wherein the hydrogenation catalyst comprises ruthenium and a solid support.

7. A method for synthesizing homoserine, the method comprising:
reacting erythronic acid in a reaction mixture under hydrogen pressure and comprising an aminating agent, to form homoserine.

8. The method of claim 7, further comprising reacting the homoserine with a mercaptan compound to produce methionine.

9. The method of claim 7, wherein the erythronic acid is dehydrated to produce a corresponding dicarbonyl intermediate, with a portion of the dicarbonyl intermediate being reductively aminated to produce homoserine and further comprising cracking another portion of the dicarbonyl intermediate to form pyruvic acid and reductively aminating the pyruvic acid to produce alanine.

* * * * *